(12) United States Patent
Heuer et al.

(10) Patent No.: US 7,358,326 B2
(45) Date of Patent: Apr. 15, 2008

(54) MULTIFUNCTIONAL 3,4-ALKYLENEDIOXYTHIOPHENE DERIVATIVES AND ELECTRICALLY CONDUCTIVE POLYMERS CONTAINING THEM

(75) Inventors: Helmut-Werner Heuer, Krefeld (DE); Rolf Wehrmann, Krefeld (DE)

(73) Assignee: H.C. Starck GmbH (DE)

( * ) Notice: Subject to any disclaimer, the term of this patent is extended or adjusted under 35 U.S.C. 154(b) by 85 days.

(21) Appl. No.: 11/005,211

(22) Filed: Dec. 6, 2004

(65) Prior Publication Data

US 2005/0131204 A1 Jun. 16, 2005

(30) Foreign Application Priority Data

Dec. 10, 2003 (DE) ............................ 103 57 571

(51) Int. Cl.
*C08G 75/32* (2006.01)
*C08G 75/00* (2006.01)
*C08G 61/00* (2006.01)
*C08G 61/12* (2006.01)

(52) U.S. Cl. ...................... 528/373; 528/377; 528/378; 528/380; 549/50

(58) Field of Classification Search ................. 528/373, 528/377, 378, 380; 549/50
See application file for complete search history.

(56) References Cited

OTHER PUBLICATIONS

Database CA 'Online? Chemical Abstracts Service, Columbus, Ohio, US; Shirato, Kentaro et al: Photoelectric converters and solar cells XP002321715 gefunden im STN Database accession No. 2001:225754 Zusammenfassung & JP 2001 085713 A2 (Fuji Photo Film Co., Ltd., Japan) Mar. 30, 2001.
Database CA 'Online? Chemical Abstracts Service, Columbus Ohio, US; Sankaran, Balasubramanian et al: "Thiophene-based branced conjugated polymers" XP002321716 gefunden im STN Database accession No. 2001:221126 Zusammenfassung & Polymer Preprints (American Chemical Society, Division of Polymer Chemistry), 42(1), 602-603 Coden: ACPPAY; ISSN: 0032-3934, 2001.

Sonmez G et al: "A Highly Stable, New Electrochromic Polymer: Poly(1,4-Bis(2-(3',4'-Ethylenedioxy)Thienyl)-2-Methoxy-5-2-Ethylhexyl Oxybenzene)" Advanced Functional Materials, Wiley Intersciences, Wienheim, DE, Bd. 13, Nr. 9, Aug. 2003, Seiten 726-731, XP001170465 ISSN: 1616-301X das ganze Document.

*Primary Examiner*—Duc Truong
(74) *Attorney, Agent, or Firm*—Connolly Bove Lodge & Hutz LLP

(57) ABSTRACT

Multifunctional 3,4-alkylenedioxythiophene derivatives represented by formula (I) are described,

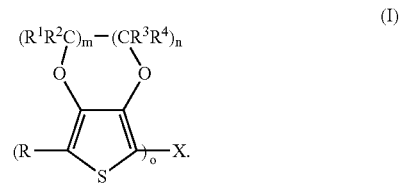

In formula (I), n and m each independently of each other, and independently for each o, are an integer from 1 to 5, and o is 3 or 4. The groups $R^1$, $R^2$, $R^3$ and $R^4$ are independently of each other and independently for each o, selected from, for example, hydrogen, halogen and optionally substituted linear or branched $C_1$-$C_{20}$-alkyl. The group R— of formula (I) may be, independently for each o, hydrogen or a thiophene represented by the following formula (II),

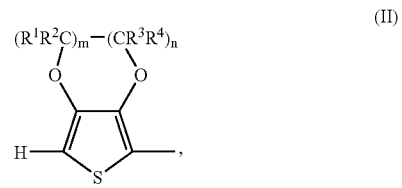

in which m, n, $R^1$, $R^2$, $R^3$ and $R^4$ are as described in formula (I). The group X— of formula (I) is a polyvalent linking unit (e.g., a triphenylamine radical). Also described are electrically conductive oligomers and polymers comprising the multifunctional 3,4-alkylenedioxythiophene derivatives of the present invention as a repeating or crosslinking unit.

10 Claims, No Drawings

MULTIFUNCTIONAL 3,4-ALKYLENEDIOXYTHIOPHENE DERIVATIVES AND ELECTRICALLY CONDUCTIVE POLYMERS CONTAINING THEM

CROSS REFERENCE TO RELATED PATENT APPLICATION

The present patent application claims the right of priority under 35 U.S.C. §119 (a)-(d) of German Patent Application No. 103 57 571.5, filed Dec. 10, 2003.

FIELD OF THE INVENTION

The invention relates to multifunctional 3,4-alkylenedioxythiophene derivatives, to a process for their preparation and to their use in the preparation of electrically conductive oligomers and polymers, such as long-chain branched oligomers and long-chain branched polymers. The invention relates also to oligomers or polymers containing these compounds as repeating units or as crosslinking units, e.g., long-chain branched electrically conductive polymers.

BACKGROUND OF THE INVENTION

Organic conductive polymers have a broad spectrum of applications. Examples of such applications include their use in the production of polymer batteries, of diodes or transistors or of solar cells, as well as the production of capacitors, of organic or inorganic light-emitting diodes, ITO or TCO replacement (ITO=indium-tin oxide, TCO=transparent conductive oxide), displays such as LCDs or PDLCs or electrochromic devices. Further applications include, for example, corrosion prevention, antistatics, sensor technology, and also as a hole-injection and brightening coating on TCO substrates. Systems based on polyacetylene, poly(p-phenylene), polythiophene or polypyrrole, for example, are used as organic conductive polymers.

Some known electrically conductive oligomers and polymers are prepared from thiophene derivatives. A particular example is poly[3,4-ethylenedioxythiophene] (PEDT), which is used in particular in the cationic form with poly-styrenesulfonic acid (PSS) as a further anionic component. PEDT-PSS is commercially available under the name Baytron® P electrically conductive polymer.

SUMMARY OF THE INVENTION

In order to enable the polymer properties, especially the degree of polymerisation, the film-forming properties and the solubility and conductivity of the polymer, to be adjusted to particular demands in a targeted manner, it is necessary to have available a large number of monomeric structural units. The degree of polymerisation can be influenced particularly effectively by the incorporation of branching or crosslinking sites into the polymer. The object of the present invention is therefore to provide novel multifunctional thiophene derivatives which are able to act as branching or crosslinking sites in polymers. By using these multifunctional thiophene structural units in admixture with conventional bifunctional structural units it is possible to prepare short-chain branched and long-chain branched electrically conductive polymers from the copolymerisation.

The term "long-chain branched" is here understood as meaning electrically conductive polymers that have extending from the polymer main chain side chains which may correspond to the length of the polymer main chain in respect of the order of magnitude of length. Short-chain branched polymers, on the other hand, exhibit only relatively short side chains grafted on to the polymer main chain.

These types of branched electrically conductive polymers based on multifunctional 3,4-alkylenedioxythiophene derivatives have not been described hitherto.

In light of the present invention, it is now possible to prepare multi functional. 3,4-alkylenedioxythiophene derivatives, in which three or four 3,4-alkylene-dioxythiophene radicals are bonded to a common linking unit.

In accordance with the present invention, there is provided a compound represented by the following formula (I),

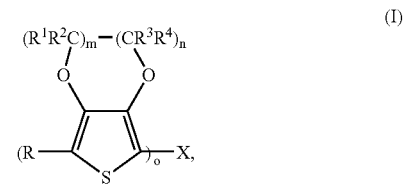

wherein n and m each independently of the other, and independently for each o, represents an integer from 1 to 5, o represents 3 or 4, $R^1$, $R^2$, $R^3$ and $R^4$ each independently of the others, and independently for each o, represents hydrogen, halogen, optionally substituted $C_1$-$C_{20}$-alkyl, hydroxyl, an optionally substituted ester radical —$(CH_2)_p$—O—CO—$C_qH_{2q+1}$, an optionally substituted ether radical —$(CH_2)_p$—O—$C_qH_{2q+1}$, an optionally substituted radical —$(CH_2)_p$—O—$C_qH_{2q}SO_3Na$, an optionally substituted oligoethylene glycol radical —$(CH_2)_p$—O—$(CO)_r$—$(CH_2CH_2O)_sCH_3$ or a radical containing a mesogenic group, or $R^1$, $R^2$, $R^3$ and $R^4$ together represent a crown ether structure, wherein the optional substituents are selected from, for example, hydroxyl, halogen (e.g., F, Cl, Br and I), linear or branched $C_1$-$C_6$ alkyl (e.g., methyl, ethyl, n-propyl, i-propyl, n-butyl, i-butyl, t-butyl, pentyl and hexyl), $C_5$-$C_8$ cycloalkyl (e.g., cyclopentyl, cyclohexyl, cycloheptyl and cyclooctyl) and aryl (e.g., phenyl), further wherein

| | |
|---|---|
| p | in each case represents an integer from 0 to 6, |
| q | in each case represents an integer from 1 to 20, |
| r | represents 0 or 1, and |
| s | represents an integer from 1 to 20, | and

R represents, and independently for each o, hydrogen or a thiophene of formula (II)

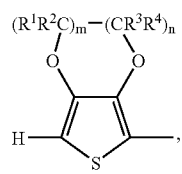

(II)

wherein m, n, $R^1$, $R^2$, $R^3$ and $R^4$ are as defined in formula (I), and

X represents a polyvalent linking unit (having a linking valency equivalent to that of subscript-o, i.e., of 3 or 4).

Other than in the operating examples, or where otherwise indicated, all numbers expressing quantities of ingredients, reaction conditions, and so forth used in the specification and claims are to be understood as modified in all instances by the term "about."

The term "substituted" above and below means in particular, if not otherwise indicated, halogen substituted. Particularly preferred "substituted" means a substitution with F, Cl or Br in particular with F.

DETAILED DESCRIPTION OF THE INVENTION

With reference to formulas (I) and (II), n and m each preferably represent 1.

$R^1$, $R^2$, $R^3$ and $R^4$ each independently of the others preferably represents hydrogen, halogen, preferably fluorine or chlorine, $C_1$-$C_{14}$-alkyl, $CH_2OH$, $CH_2O(CO)C_tHal_{2t+1}$, $CH_2OC_tH_{2t+1}$, $CH_2OC_tHal_{2t+1}$, $CH_2O(CH_2CH_2O)_tCH_3$ or $CH_2O(CH_2)_tSO_3Na$, wherien t in each case represents an integer from 1 to 20 and Hal represents halogen, preferably fluorine.

$R^1$, $R^2$, $R^3$ and $R^4$ particularly preferably represent hydrogen.

R preferably represents hydrogen.

Accordingly, the thiophene unit is particularly preferably a 3,4-ethylenedioxythiophene unit.

The linking unit X may be any unit to which 3- or 4-thiophene units can be chemically bonded. Examples which may be mentioned include $C_5$-$C_{14}$-aryl, $C_{12}$-$C_{20}$-biaryl, optionally substituted triarylamine and optionally substituted triarylphosphane.

In a particular embodiment, o represents 3 and the linking unit X is a benzene radical or a triphenylamine radical.

In a further embodiment, o represents 4 and the linking unit X is a biphenyl radical.

The multifunctional, 3,4-alkylenedioxythiophene derivative according to the invention is particularly preferably a compound of formula (III)

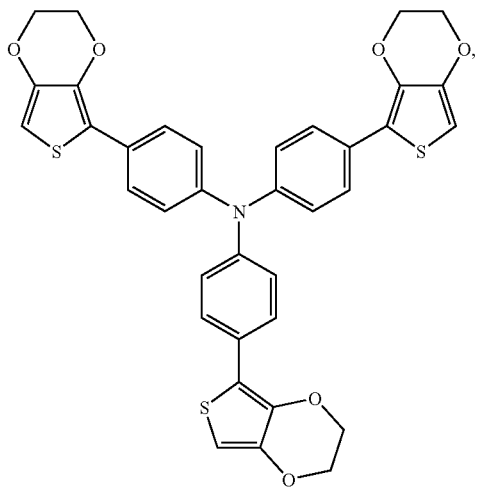

(III)

a compound of formula (IV)

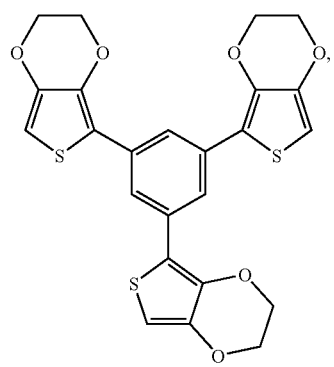

(IV)

or a compound of formula (V)

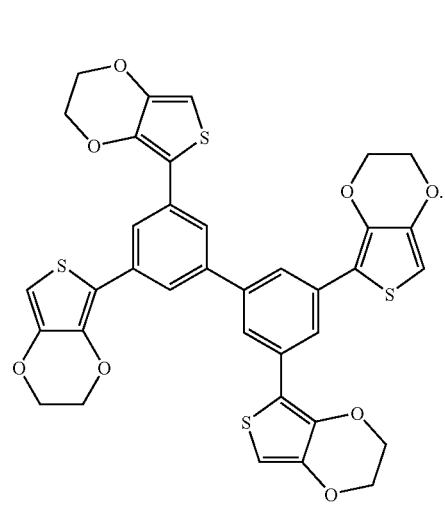

(V)

Compounds of formulae (I), (III), (IV) and (V) can be prepared, for example, by reaction of suitable thiophenes with a halo-substituted linking unit.

First of all, for example, the desired thiophene derivative of formula (VII)

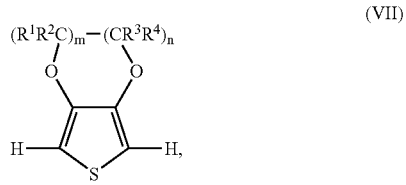

(VII)

wherein m, n, $R^1$, $R^2$, $R^3$ and $R^4$ are as defined above, is converted by reaction with, for example, about one molar equivalent of base, for example tert-butyllithium, into the monolithium compound, and the latter is then converted, by reaction with a trialkyltin halide, preferably with trimethyltin bromide, trimethyltin chloride, tri-tert-butyltin bromide or tri-tert-butyltin chloride, into a compound of formula (VIII)

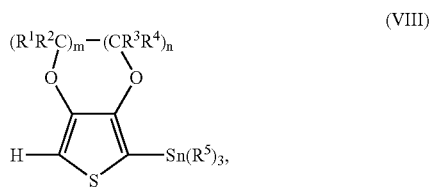

(VIII)

wherein m, n, $R^1$, $R^2$, $R^3$ and $R^4$ are as defined above and $R^5$ represents $C_1$-$C_{10}$-Alkyl.

$R^5$ preferably represents methyl or tert-butyl.

The compound of formula (VIII) can be reacted, for example, in the presence of a Pd(0) catalyst with a halo-substituted linking unit to form the desired product of formula (I).

This reaction can be carried out, for example, in dipolar, aprotic solvents, such as, for example, N-methyl-2-pyrrolidone (NMP), dimethylformamide, dimethylacetamide, dimethyl sulfoxide or high-boiling ketones. Dimethylformamide is preferably used as the solvent.

The reaction can be carried out, for example, at a temperature of from 20 to 150° C. The reaction is preferably carried out at normal pressure. It is, however, also possible to work under elevated pressure.

The compounds of formulae (I), (III), (IV) and (V) can be used in the preparation of electrically conductive oligomers and polymers. It is possible either to use only one of these compounds as monomer or to use a mixture of different compounds that fall within the definition of formulae (I), (III), (IV) and/or (V).

If only compounds of formulae (I), (III), (IV) and/or (V) are used as monomer, then highly branched network structures are obtained.

However, the compounds of formulae (I), (III), (IV) and/or (V) are preferably not used in the preparation of electrically conductive oligomers and polymers that are composed solely of such units, but are introduced in a targeted manner as crosslinking units in the preparation of electrically conductive oligomers and polymers that, in addition to containing one or more compounds of formulae (I), (III), (IV) and/or (V), also contain further, difunctional thiophene derivatives as monomers, especially 3,4-ethylenedioxythiophene. The degree of crosslinking of the oligomer or polymer is dependent especially on the molar ratio of the multifunctional 3,4-alkylenedioxythiophene derivatives according to the invention to the amount of difunctional thiophene derivatives used and can be adjusted accordingly by the choice of molar ratio.

The polymerisation is carried out according to the procedure employed in the polymerisation of known thiophene derivatives. It may be carried out, for example, oxidatively by means of oxidising agents such as iron(III) chloride or other iron(III) salts, $H_2O_2$, sodium or potassium peroxodisulfate, potassium dichromate, potassium permanganate, or electrochemically.

The invention therefore relates also to the use of compounds of formulae (I), (III), (IV) and/or (V) in the preparation of electrically conductive oligomers and polymers, and to electrically conductive oligomers and polymers prepared by polymerisation using such a compound.

The invention relates especially to electrically conductive multi-mers (i.e., oligomers and/or polymers) that contain as repeating or crosslinking units structural units of formula (VI)

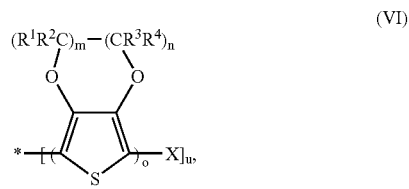

(VI)

wherein n, m, o, $R^1$, $R^2$, $R^3$ and $R^4$ and X are as defined previously herein with reference to formula (I), and u represents an integer from 1 to 500.

At the * marked position further other monomers can be polymerized e.g. in the case of Copolymers.

Preferably, u represents from 1 to 400, particularly preferably from 1 to 300.

Particular preferred are copolymers on the basis of a monomer, which forms electrically conductive polymers, in particular of an optionally substituted thiophen, particularly preferred of 3,4-ethylene dioxythiophen, said polymers having structural units of formula VI.

The structural units of formula VI may be neutral, as shown in the formula. It is also possible, however, for them to carry a positive charge. In this case, the new polymers will get anions as counter-ions. These anions are in turn preferably polymeric in structure; the polyanions are particularly preferably polystyrene sulfonate.

The oligomers and polymers according to the invention are suitable for many different applications and can be used, for example, in a very wide variety of electronics products. Examples which may be mentioned include their use in the production of polymer batteries, of diodes, photodiodes or transistors, for example field-effect transistors, or of solar cells, as well as capacitors, especially as electrode material in solid-electrolyte capacitors, organic or inorganic light-emitting diodes which make use of the principle of electroluminescence or electrophosphorescence, ITO and TCO replacement (TCO=transparent conductive oxide), displays such as LCDs or PDLCs, electrochromic devices, in articles sensor technology manufacture, and transparent conductive mono- and multi-layer films.

Further applications are corrosion prevention, antistatics and use as a hole-injection and brightening coating on TCO substrates or as a conductive printing paste and ink-jet formulation. The oligomers or polymers according to the invention may further be used as membranes, in the production of rechargeable polymer batteries or of coatings on paper for low-cost electronics applications or as substrates for currentless deposition.

The present invention is more particularly described in the following examples, which are intended to be illustrative only, since numerous modifications and variations therein will be apparent to those skilled in the art. Unless otherwise specified, all parts and percentages are by weight.

EXAMPLES

Example 1

An oligomeric compound accoding to the present invention was prepared in accordance with the following representative synthetic pathway diagram, and as further described herein.

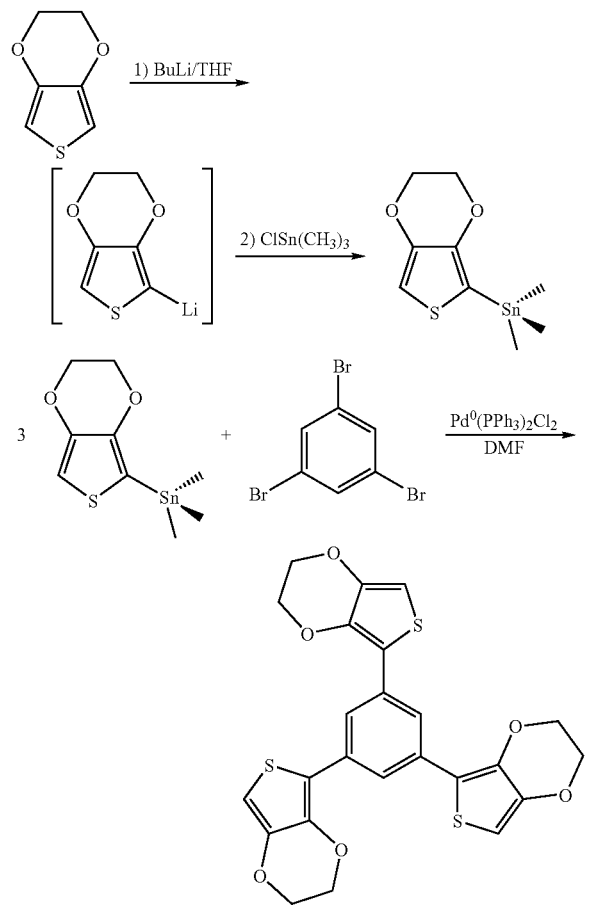

12.78 g (90 mmol.) of 3,4-ethylenedioxythiophene (Baytron® M, Bayer AG, Leverkusen) were placed in 100 ml of dry tetrahydrofuran (THF). After cooling to −67° C., 39 ml of a 15 wt. % butyllithium (BuLi) solution in n-hexane were added in portions under argon protecting gas. When the addition was complete, stirring was carried out for a further hour, with cooling. 17.94 g (90 mmol.) of trimethyltin chloride (Aldrich) in 90 ml of dry THF were then added. Stirring was then carried out for 30 minutes, with cooling, and the reaction batch was then allowed to warm to room temperature. For working up, 200 ml of methylene chloride were added. The last residues of organometallic compounds were quenched by addition of 100 ml of water. The organic phase was then washed with water and dried over sodium sulfate. After separating off the solvent in vacuo, 21.5 g of crude product were obtained and were stored in a refrigerator in order to allow the product to crystallise out. 11.5 g of a solid (yield: 41.9% of theory) were obtained as the product.

Analysis by means of gas chromatography-mass spectrometry (GC-MS) showed a signal at a molecular mass of 305, corresponding to the molecular weight of the desired silylated 3,4-ethylenedioxythiophene. The doubly silylated product was obtained as secondary product.

The analogous reaction was repeated using the following weighed portions:

20.19 g (141.9 mmol.) of 3,4-ethylenedioxythiophene in 150 ml of THF 60 ml of 15 wt. % BuLi in n-hexane 28.35 g (141.9 mmol.) of trimethyltin chloride.

42.0 g of crude product were obtained.

10.0 g (32.8 mmol.) of the silylated 3,4-ethylenedioxythiophene were dissolved in 100 ml of dry N,N-dimethylformamide (DMF) under argon protecting gas, and there were added thereto 3.44 g (10.9 mmol.) of 1,3,5-tribromobenzene (Aldrich) and 1.0 g (1.4 mmol.) of bis-(triphenylphosphine)-palladium(II) chloride as catalyst of the Stille reaction. After repeated degassing of the yellow suspension, the mixture was heated to 100° C. and the temperature was maintained for 15 hours. For working up, the solvent DMF was separated off in vacuo and the residue was chromatographed on silica gel.

0.6 g (yield: 11% of theory) of yellow solid was obtained as the product.

There was additionally obtained as a further fraction 0.1 g of a green solid which, as secondary product, had the following structure, with a molecular weight of 714.8 (GC-MS):

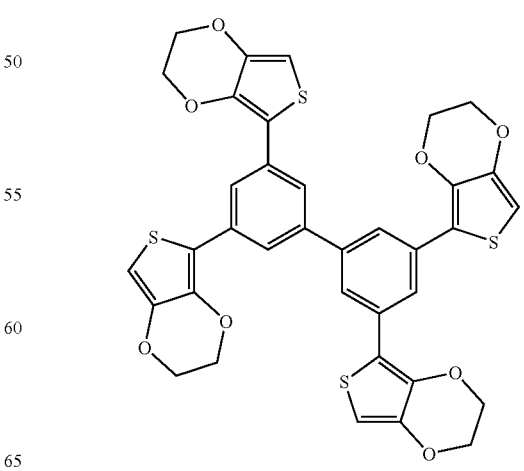

Traces of the following structures could also be detected:

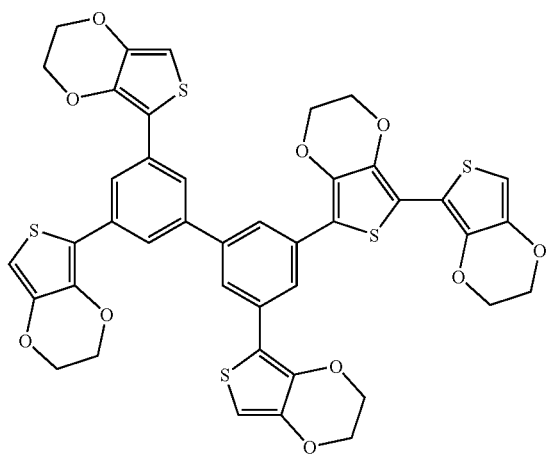

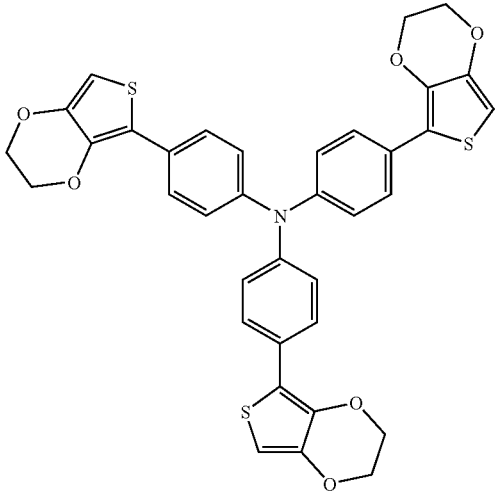

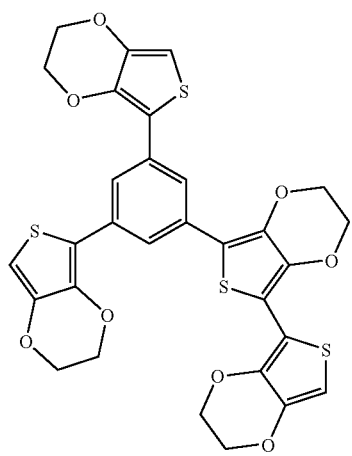

Example 2

An oligomeric compound accoding to the present invention was prepared in accordance with the following representative synthetic pathway diagram, and as further described herein.

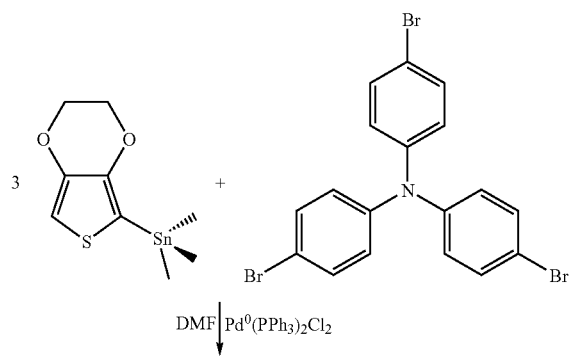

Analogously to the coupling reaction of Example 1, 10.0 g (32.8 mmol.) of the silylated 3,4-ethylenedioxythiophene from Example 1 in 100 ml of dry DMF were reacted with 5.25 g (10.9 mmol.) of tris-(4-bromophenyl)amine (Aldrich) and 1.0 g (1.4 mmol.) of bis-(triphenylphosphine)-palladium (II) chloride. The reaction mixture was heated for 22.5 hours at 100° C. The solvent was separated off, followed by chromatography on silica gel. 0.6 g of a green solid was obtained, which was the desired product with the expected molecular mass of 665 (mass spectrometry).

Example 3

0.025 g (0.05 mmol.) of the product from Example 1 was potentiostatically electropolymerised on indium-tin oxide (ITO) on glass by oxidation at 3.5 volts in 5 ml of dry, degassed acetonitrile with 0.171 g (0.5 mmol.) of tetrabutylammonium perchlorate as the conducting salt. A purplish/reddish brown polymeric film was thereby deposited on the ITO. After drying, the polymeric, branched network had a dark-brownish red colour.

Example 4

0.0357 g (0.05 mmol.) of the tetrafunctional secondary product of mass 714.8 from Example 1 was electropolymerised in a manner analogous to that indicated in Example 3. Here too, a polymeric network having a dark-brownish red colour was obtained after drying.

Example 5

0.015 g (0.03 mmol.) of the product from Example 1 (3 mol. %) and 0.142 g (1 mmol.) of 3,4-ethylenedioxythiophene (97 mol. %) were electropolymerised in a manner analogous to that described in Example 3 in 100 ml of acetonitrile with 4.4 g (10 mmol.) of tetrabutylammonium perchlorate. A bright metallic greyish brown polymer was obtained.

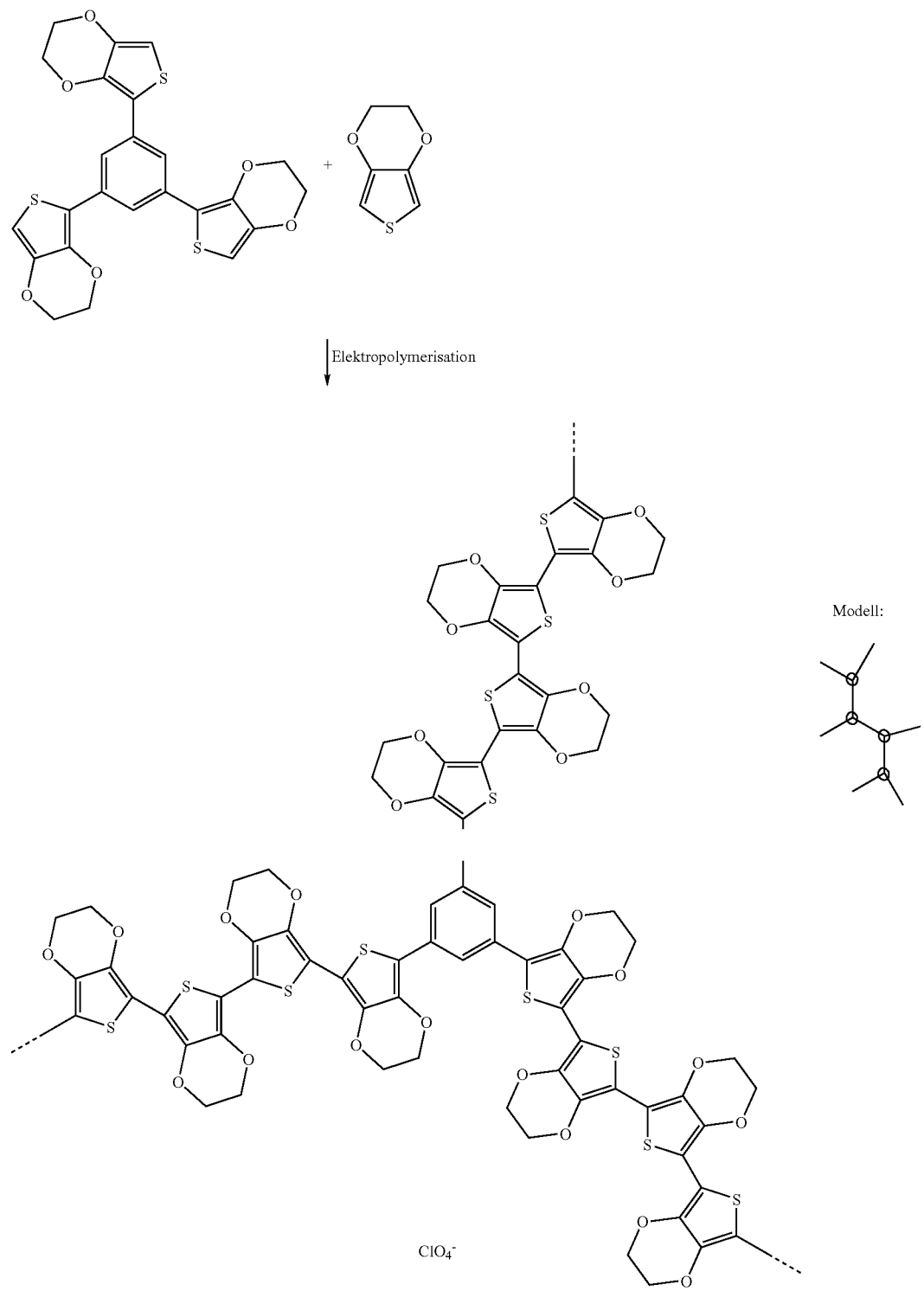
Example 6
0.0214 g (0.03 mmol.) of the secondary product from Example 1 (3 mol. %) and 0.142 g (1 mmol.) of 3,4-ethylenedioxythiophene (97 mol. %) were electropolymerised in a manner analogous to that described in Example 3 in 100 ml of acetonitrile with 4.4 g (10 mmol.) of tetrabutylammonium perchlorate. A bright metallic dark-greyish violet polymer was obtained.

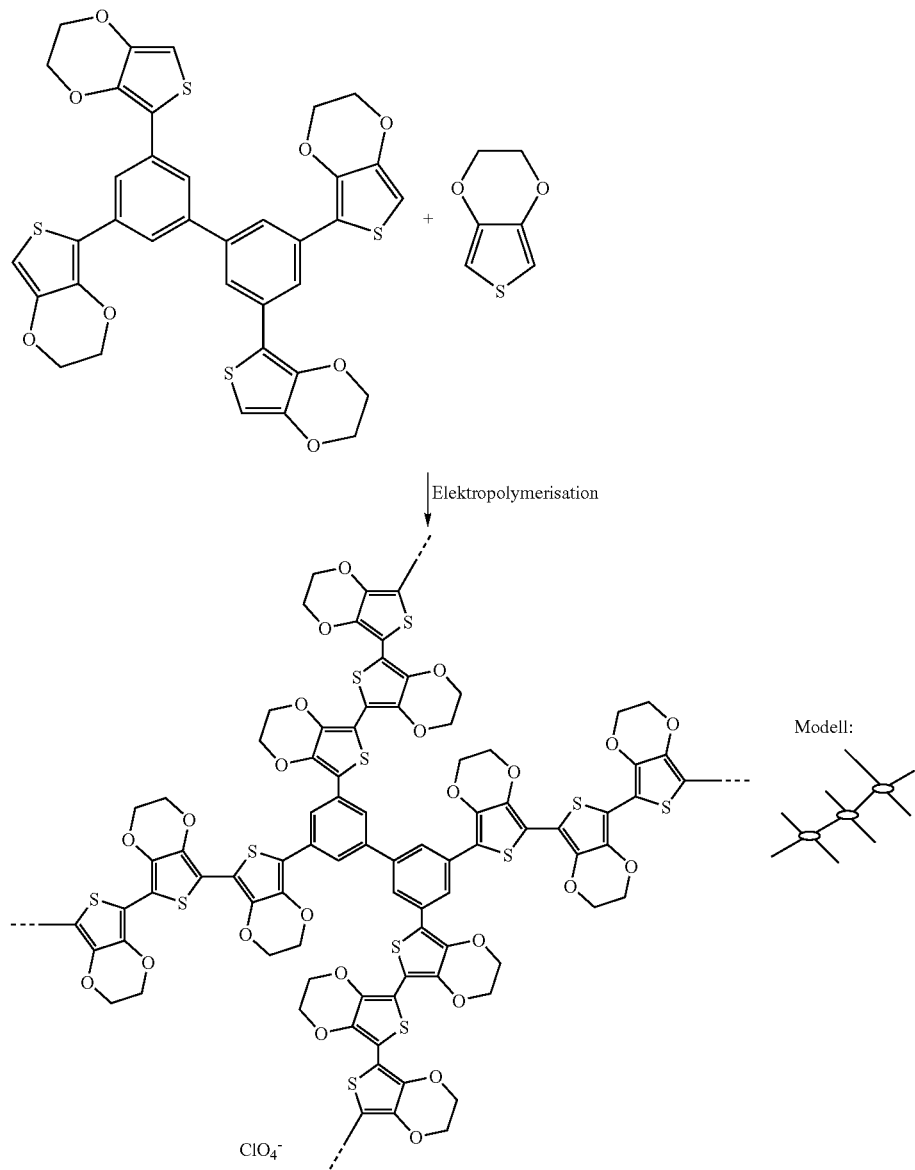

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound represented by the following formula (I),

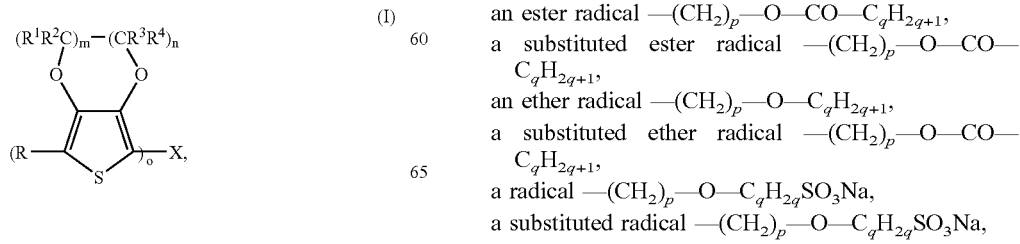

wherein n and m each independently of each other, and independently for each o, is an integer from 1 to 5, o is 3 or 4, $R^1$, $R^2$, $R^3$ and $R^4$ each independently of each other, and independently for each o, are selected from a member of the group consisting of hydrogen, halogen, linear or branched $C_1$-$C_{20}$-alkyl, linear or branched substituted $C_1$-$C_{20}$-alkyl hydroxyl, an ester radical —$(CH_2)_p$—O—CO—$C_qH_{2q+1}$, a substituted ester radical —$(CH_2)_p$—O—CO—$C_qH_{2q+1}$, an ether radical —$(CH_2)_p$—O—$C_qH_{2q+1}$, a substituted ether radical —$(CH_2)_p$—O—CO—$C_qH_{2q+1}$, a radical —$(CH_2)_p$—O—$C_qH_{2q}SO_3Na$, a substituted radical —$(CH_2)_p$—O—$C_qH_{2q}SO_3Na$, an oligoethylene glycol radical —$(CH_2)_p$—O—$(CO)_r$—$(CH_2CH_2O)_sCH_3$,
a substituted oligoethylene glycol radical —$(CH_2)_p$—O—$(CO)_r$—$(CH_2CH_2O)_sCH_3$,
a radical containing a mesogenic group,
and $R^1$, $R^2$, $R^3$ and $R^4$ together forming a crown ether structure,
  wherein the substituents of the substituted members, from which $R^1$, $R^2$, $R^3$ and $R^4$, may each be independently selected, are selected independently from the group consisting of hydroxyl, halogen, linear or branched $C_1$-$C_6$ alkyl, $C_5$-$C_8$ cycloalkyl and aryl,
wherein
  p in each case represents an integer from 0 to 6,
  q in each case represents an integer from 1 to 20,
  r represents 0 or 1, and
  s represents an integer from 1 to 20, and
R is selected, independently for each o, from the group consisting of hydrogen and a thiophene represented by the following formula (II)

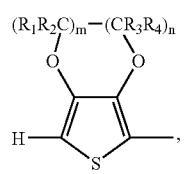

(II)

wherein
m, n, are as defined in formula (I),
$R_2$, $R_3$ and $R_4$ each independently of each other, and independently for each o, are selected from a member of the group consisting of hydrogen, halogen,
linear or branched $C_1$-$C_{20}$-alkyl,
linear or branched substituted $C_1$-$C_{20}$-alkyl hydroxyl,
an ester radical —$(CH_2)_p$—O—CO—$C_qH_{2q+1}$,
a substituted ester radical —$(CH_2)_p$—O—CO—$C_qH_{2q+1}$,
an ether radical —$(CH_2)_p$—O—$C_qH_{2q+1}$,
a substituted ether radical —$(CH_2)_p$—O—CO—$C_qH_{2q+1}$,
a radical —$(CH_2)_p$—O—$C_qH_{2q}SO_3Na$,
a substituted radical —$(CH_2)_p$—O—$C_qH_{2q}SO_3Na$,
an oligoethylene glycol radical —$(CH_2)_p$—O—$(CO)_r$—$(CH_2CH_2O)_sCH_3$,
a substituted oligoethylene glycol radical —$(CH_2)_p$—O—$(CO)_r$—$(CH_2CH_2O)_sCH_3$,
a radical containing a mesogenic group,
$R_1$ independently for each o, are selected from a member of the group consisting of halogen,
linear or branched $C_1$-$C_{20}$-alkyl,
linear or branched substituted $C_1$-$C_{20}$-alkyl hydroxyl,
an ester radical —$(CH_2)_p$—O—CO—$C_qH_{2q+1}$,
a substituted ester radical —$(CH_2)_p$—O—CO—$C_qH_{2q+1}$,
an ether radical —$(CH_2)_p$—O—$C_qH_{2q+1}$,
a substituted ether radical —$(CH_2)_p$—O—CO—$C_qH_{2q+1}$,
a radical —$(CH_2)_p$—O—$C_qH_{2q}SO_3Na$,
a substituted radical —$(CH_2)_p$—O—$C_qH_{2q}SO_3Na$,
an oligoethylene glycol radical —$(CH_2)_p$—O—$(CO)_r$—$(CH_2CH_2O)_sCH_3$,
a substituted oligoethylene glycol radical —$(CH_2)_p$—O—$(CO)_r$—$(CH_2CH_2O)_sCH_3$,
a radical containing a mesogenic group, and
X represents a polyvalent linking unit selected from the group of $C_5$-$C_{14}$-aryl, $C_{12}$-$C_{20}$-diaryl, substituted or non-substituted triarylamine and substituted or non-substituted triaryiphosphane.

2. The compound of claim 1 wherein n and m are each 1.

3. The compound of claim 1 wherein $R^1$, $R^2$, $R^3$ and $R^4$ are each hydrogen.

4. The compound of claim 1 wherein R is hydrogen.

5. The compound of claim 1 wherein o represents 3, and the linking unit X is selected from the group consisting of benzene radicals and triphenylamine radicals.

6. The compound of claim 1 wherein o represents 4, and the linking unit X is a biphenyl radical.

7. A compound represented by the following formula (I),

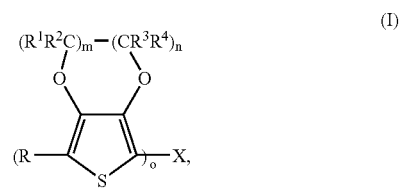

(I)

wherein
n and m each independently of each other, and independently for each o, is an integer from 1 to 5,
o is 3,
$R^1$, $R^2$, $R^3$ and $R^4$ each independently of each other, and independently for each o, are selected from a member of the group consisting of hydrogen, halogen,
linear or branched $C_1$-$C_{20}$-alkyl,
linear or branched substituted $C_1$-$C_{20}$-alkyl hydroxyl,
an ester radical —$(CH_2)_p$—O—CO—$C_qH_{2q+1}$,
a substituted ester radical —$(CH_2)_p$—O—CO—$C_qH_{2q+1}$,
an ether radical —$(CH_2)_p$—O—$C_qH_{2q+1}$,
a substituted ether radical —$(CH_2)_p$—O—CO—$C_qH_{2q+1}$,
a radical —$(CH_2)_p$—O—$C_qH_{2q}SO_3Na$,
a substituted radical —$(CH_2)_p$—O—$C_qH_{2q}SO_3Na$,
an oligoethylene glycol radical —$(CH_2)_p$—O—$(CO)_r$—$(CH_2CH_2O)_sCH_3$,
a substituted oligoethylene glycol radical —$(CH_2)_p$—O—$(CO)_r$—$(CH_2CH_2O)_sCH_3$,
a radical containing a mesogenic group,
and $R^1$, $R^2$, $R^3$ and $R^4$ together forming a crown ether structure,
  wherein the substituents of the substituted members, from which $R^1$, $R^2$, $R^3$ and $R^4$, may each be independently selected, are selected independently from the group consisting of hydroxyl, halogen, liner or branched $C_1$-$C_6$ alkyl, $C_5$-$C_8$ cycloalkyl and aryl,
wherein
  p in each case represents an integer from 0 to 6,
  q in each case represents an integer from 1 to 20,
  r represents 0 or 1, and
  s represents an integer from 1 to 20, and
R is selected, independently for each o, from the group consisting of hydrogen and a thiophene represented by the following formula (II),

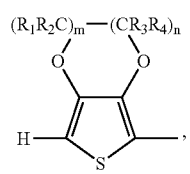
(II)

wherein m, n, are as defined in formula (I), $R_1$, $R_2$, $R_3$ and $R_4$ each independently of each other, and independently for each o, are selected from a member of the group consisting of hydrogen, halogen, linear or branched $C_1$-$C_{20}$-alkyl, linear or branched substituted $C_1$-$C_{20}$-alkyl hydroxyl, an ester radical —$(CH_2)_p$—O—CO—$C_qH_{2q+1}$, a substituted ester radical —$(CH_2)_p$—O—CO—$C_qH_{2q+1}$, an ether radical —$(CH_2)_p$—O—$C_qH_{2q+1}$, a substituted ether radical —$(CH_2)_p$—O—CO—$C_qH_{2q+1}$, a radical —$(CH_2)_p$—O—$C_qH_{2q}SO_3Na$, a substituted radical —$(CH_2)_p$—O—$C_qH_{2q}SO_3Na$, an oligoethylene glycol radical —$(CH_2)_p$—O—$(CO)_r$—$(CH_2CH_2O)_sCH_3$, a substituted oligoethylene glycol radical —$(CH_2)_p$—O—$(CO)_r$—$(CH_2CH_2O)_sCH_3$, a radical containing a mesogenic group, and the linking unit X is a triphenylamine radical, and said compound is represented by the following formula (III),

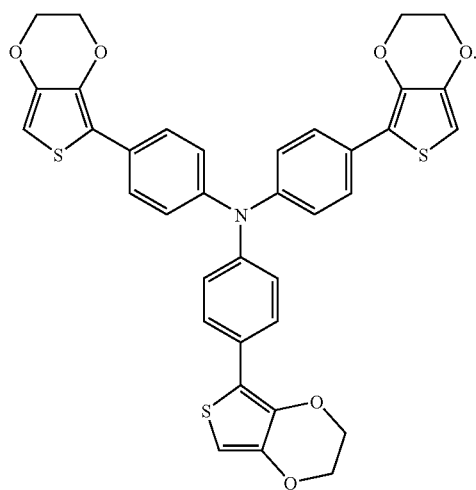
(III)

8. The compound of claim 5 wherein the linking unit X is a benzene radical, and said compound is represented by the following formula (IV),

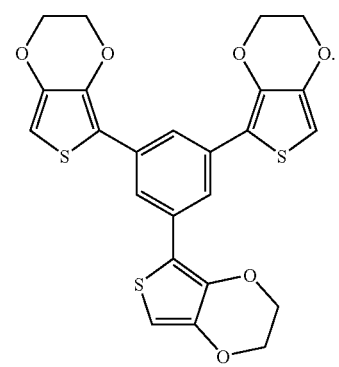
(IV)

9. The compound of claim 6 wherein said compound is represented by the following formula (V),

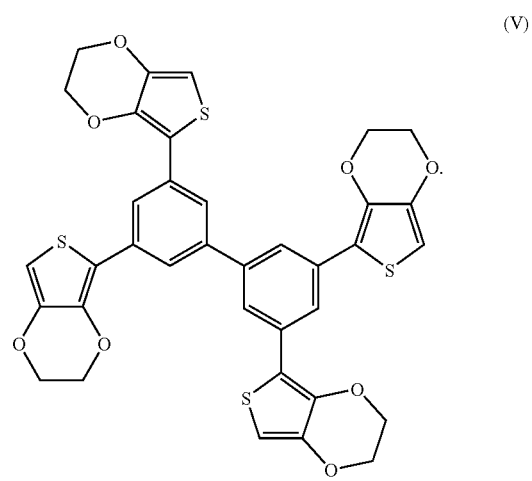
(V)

10. A compound represented by the following formula (I),

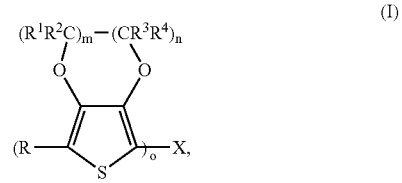
(I)

wherein n and m each independently of each other, and independently for each o, is an integer from 1 to 5, o is 3 or 4, $R^1$, $R^2$, $R^3$ and $R^4$ each independently of each other, and independently for each o, are selected from a member of the group consisting of hydrogen, halogen, linear or branched $C_1$-$C_{20}$-alkyl, linear or branched substituted $C_1$-$C_{20}$-alkyl hydroxyl, an ester radical —$(CH_2)_p$—O—CO—$C_qH_{2q+1}$, a substituted ester radical —$(CH_2)_p$—O—CO—$C_qH_{2q+1}$, an ether radical —$(CH_2)_p$—O—$C_qH_{2q+1}$, a substituted ether radical —$(CH_2)_p$—O—CO—$C_qH_{2q+1}$,
a radical —$(CH_2)_p$—O—$C_qH_{2q}SO_3Na$,
a substituted radical —$(CH_2)_p$—O—$C_qH_{2q}SO_3Na$,
an oligoethylene glycol radical —$(CH_2)_p$—O—$(CO)_r$—$(CH_2CH_2O)_sCH_3$,
a substituted oligoethylene glycol radical —$(CH_2)_p$—O—$(CO)_r$—$(CH_2CH_2O)_sCH_3$,
a radical containing a mesogenic group,
and $R^1$, $R^2$, $R^3$ and $R^4$ together forming a crown ether structure,
  wherein the substituents of the substituted members, from which $R^1$, $R^2$, $R^3$ and $R^4$, may each be independently selected, are selected independently from the group consisting of hydroxyl, halogen, liner or branched $C_1$-$C_6$ alkyl, $C_5$-$C_8$ cycloalkyl and aryl,
wherein
  p in each case represents an integer from 0 to 6,
  q in each case represents an integer from 1 to 20,
  r represents 0 or 1, and
  s represents an integer from 1 to 20, and R is selected, independently for each o, from the group consisting of hydrogen and a thiophene represented by the following formula (II),

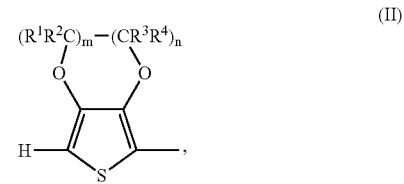

wherein
m, n, $R^1$, $R^2$, $R^3$ and $R^4$, are as defined in formula (I), and
X represents a polyvalent linking unit selected from the group of $C_5$-$C_{14}$-aryl, $C_{12}$-$C_{20}$-diaryl, substituted triarylamine and substituted or non-substituted triaryiphosphane.

* * * * *